United States Patent [19]

Barberet et al.

[11] Patent Number: Plant 7,179

[45] Date of Patent: Mar. 6, 1990

[54] CARNATION PLANT NAMED LONPILOK

[75] Inventors: Nicole Barberet; Henri Blanc, both of Antibes, France; Antonio Di Giorgio; Renato Di Giorgio, both of San Remo, Italy

[73] Assignee: Establissements Barberet et Blanc, La Londe-Les-Maures, France

[21] Appl. No.: 315,024

[22] Filed: Feb. 24, 1989

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and distinct carnation cultivar of the standard type particularly distinguished by its profuse production of medium sized blooms having a generally white coloration but characterized by the petals having short, dark red marginal streaks which provide the blooms with an unusual, randomly spaced spots scattered over the face of each fully opened bloom, each bloom being borne singly on a relatively long, flowering stem and the plant having a recurrent blooming habit with moderately abundant foliage on strong, upright stems reaching a height of about 125 cm., at eight months of growth.

1 Drawing Sheet

BACKGROUND OF THE NEW PLANT

This new carnation cultivar originated as a seedling of a hybrid developed by us in 1985, at the nursery of Antonio and Renato Di Giorgio at San Remo, Italy, by crossing two carnation varieties selected by us from the Di Giorgio collection of carnations maintained at the said nursery for breeding purposes. This particular seedling was selected for propagation because of its generally white blooms comprising almost pure white petals, many of which are distinguished by having short, dark red streaks occurring in randomly spaced relation at the petal margins and appearing on strong, upright stems of a tall plant having excellent characteristics for commercial propagation for cut flower production. This selected seedling was propagated by us by means of cutting at the said San Remo nursery with very satisfactory results and we therefore agreed that propagation should be continued through several successive generations in order to prove to us that the novel characteristics of the selected seedling would be retained from generation to generation and its homogeneity could be assured.

Accordingly, our new carnation variety is now being propagated for commercial purposes by means of in vitro propagation and cuttings at Establissements Barberet et Blanc, Laboratoire de Physiologie Vegetale, 83250 La Londe-Les Maures, France.

DESCRIPTION OF THE DRAWING

This new standard carnation cultivar is illustrated by the accompanying photographic drawing which shows several blooming stems with flowers and buds in several stages of development with three-quarter face views of two mature blooms, the color rendition being as nearly true as to that herein specified as is reasonably possible to obtain by professional photographic procedures.

DESCRIPTION OF THE NEW PLANT

The following is a detailed description of our new carnation variety based upon observations in the Spring of 1988, of plants grown in greenhouse, as well as outside, at San Remo, Italy and at La Londe-Les Maures, France, the color designations stated herein being according to The R.H.S. Colour Chart published by The Royal Horticultural Society of London, England.

THE PLANT

Origin: Seedling.

Parentage:

*Seed parent.*—Variety No. 11.

*Pollen parent.*—Variety No. 8.

Both parents being identified in breeding records maintained at the Di Giorgio nursery office at Via Villetta 41, 18038 San Remo, Italy.

Classification:

*Botanic.*—*Dianthus caryophyllus.*

*Commercial.*—Standard Carnation.

Form: An erect bush having at least four stems emitted near the ground.

Height: Averages about 125 cm. at eight months of growth.

Main stem length: Less than 15 cm. due to pinching.

Branching: This plant branches quite well.

Growth: Vigorous, upright and rigid.

Foliage:

*Quantity.*—Moderately abundant.

*Number of leaves.*—More than 120.

*Leaf-size.*—(At the seventh node) About 12.3 cm. long and 0.8 cm. wide.

*Leaf shape.*—Oblong — Linear with curved margins.

*Texture.*—Leathery.

*Color.*—Both upper and under sides, 189-A.

*Ribs and veins.*—Hardly noticeable.

*Rachis.*—Hardly noticeable.

*Leaflets.*—None.

THE BUD

Size: Medium.

*Diameter.*—Averages about 2.2 cm.

*Length.*—Averages about 3 cm.

Shape: Spherical.

Rate of opening: Normal.

Color of petals: When sepals first divide, white. When petals begin to unfurl, the same as at full bloom.

Sepals:

*Number.*—Five to seven.
*Shape.*—Generally ovate, but joined together at the lower parts and having an acuminate apex.
*Character.*—The sepals are hooded over the bud and stand up when the flower opens.
*Color.*—Inside, 145-D. Outside, 137-B and C.
*Striae.*—Longitudinal.

Calyx:
*Shape.*—Bell-shaped.
*Size.*—Large.
*Aspect.*—Smooth.
*Splitting.*—Sometimes a little splitting occurs.

Flower stem:
*Character.*—Erect and rigid.
*Color.*—189-A.

THE FLOWER

Blooming habit: Recurrent. This plant blooms profusely in the Spring, Midseason and Fall blooming periods with a tendency to give few blooms in the Fall.

Size of flower: Medium.
*Diameter.*—Averages about 7.7 cm.
*Depth.*—Averages about 5.5 cm.

Borne: Singly on a long, strong, upright stem.

Shape: When bloom first opens, high-centered. When bloom matures, dome-shaped.

Petalage:
*Number of petals.*—Averages about sixty-five.
*Arrangement.*—Imbricated.
*Form.*—Fan-shaped with rounded edges and a little serrated at the outer end portions.
*Texture.*—Leathery.
*Aspect.*—Satiny.
*Color.*—Both inner and outer petals: Body — 155-D, many with Red (Delft Rose) marginal streaks of 46-D. Base — Greenish. Reverse side — 155-D, and streaks of Currant Red, 47-C.

Petaloids:
*Number.*—Less than four.

*Size.*—Smaller than the petals.
*Color.*—The same as the petals.

Flower stem: Cut stem length, about 77 cm., cut at tenth node.
*Character.*—Rigid and upright.
*Color.*—189-A.

Discoloration after full bloom: Very little.

Persistence: The flowers hang on and dry.

Fragrance: Perceptible.

Lasting quality: As a cut flower, at least ten days in vase keeping.

REPRODUCTIVE ORGANS

Stamens:
*Number.*—Three or four.
*Arrangement.*—Around the ovary.
*Anthers.*—Size: Less than 4 mm. Color: Whitish.
*Filaments.*—Length: Averages about 2.2 cm. Color: White.

Pistils:
*Number.*—Three or four.
*Styles.*—Length: About 1.6 cm. Color: Slightly pink.
*Stigma.*—Color: Slightly pink.

Character of ovaries: Ribbed.

This new carnation cultivar most nearly resembles the variety Arthur (unpatented). Compared to Arthur, however, this new variety has a petal which is a little more serrated and with more red marginal markings and a more rigid stem.

The expression of all of the above characteristics may be more or less strongly modulated under the environmental condition of propagation.

We claim:

1. The new and distinctive carnation cultivar substantially as herein shown and described, characterized by its blooms having pure white petals with randomly spaced medium red marginal marks.

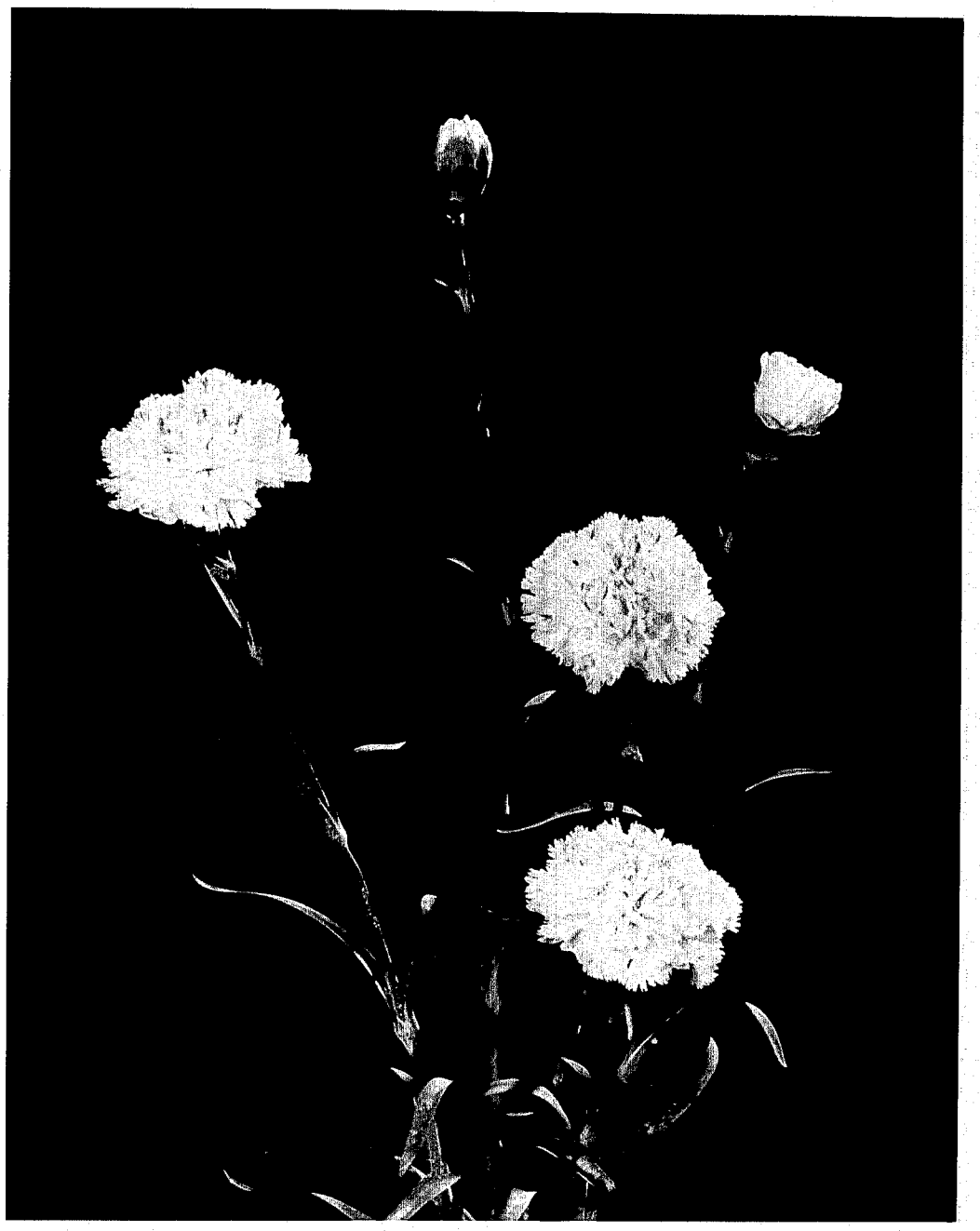

* * * * *